US011318100B2

(12) United States Patent
Sundaram (10) Patent No.: US 11,318,100 B2
(45) Date of Patent: *May 3, 2022

(54) STORAGE STABLE SINCALIDE FORMULATIONS

(71) Applicant: MAIA Pharmaceuticals, Inc., Princeton, NJ (US)

(72) Inventor: Srikanth Sundaram, Somerset, NJ (US)

(73) Assignee: MAIA Pharmaceuticals, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/397,444

(22) Filed: Aug. 9, 2021

(65) Prior Publication Data
US 2021/0361580 A1   Nov. 25, 2021

Related U.S. Application Data

(62) Division of application No. 15/958,854, filed on Apr. 20, 2018, now Pat. No. 11,110,063.

(60) Provisional application No. 62/550,484, filed on Aug. 25, 2017.

(51) Int. Cl.
| | |
|---|---|
| *A61K 9/19* | (2006.01) |
| *A61K 9/16* | (2006.01) |
| *A61P 1/18* | (2006.01) |
| *A61K 9/08* | (2006.01) |
| *A61K 38/08* | (2019.01) |
| *A61P 1/16* | (2006.01) |
| *A61K 9/00* | (2006.01) |
| *A61K 47/18* | (2017.01) |
| *A61K 47/24* | (2006.01) |
| *A61K 47/26* | (2006.01) |

(52) U.S. Cl.
CPC .............. *A61K 9/19* (2013.01); *A61K 9/0019* (2013.01); *A61K 9/08* (2013.01); *A61K 9/1611* (2013.01); *A61K 9/1617* (2013.01); *A61K 9/1682* (2013.01); *A61K 38/08* (2013.01); *A61K 47/183* (2013.01); *A61K 47/24* (2013.01); *A61K 47/26* (2013.01); *A61P 1/16* (2018.01); *A61P 1/18* (2018.01)

(58) Field of Classification Search
None
See application file for complete search history.

(56) References Cited

U.S. PATENT DOCUMENTS

| | | | |
|---|---|---|---|
| 3,723,406 A | 3/1973 | Ondetti et al. | |
| 3,937,819 A | 2/1976 | Ondetti et al. | |
| 5,011,678 A | 4/1991 | Wang et al. | |
| 5,217,954 A | 6/1993 | Foster et al. | |
| 5,272,135 A | 12/1993 | Takuri | |
| 5,461,031 A | 10/1995 | De Felippis | |
| 5,556,610 A | 9/1996 | Yan et al. | |
| 5,565,423 A | 10/1996 | Sandow et al. | |
| 5,567,414 A | 10/1996 | Schneider et al. | |
| 5,676,950 A | 10/1997 | Small, Jr. et al. | |
| 5,747,447 A | 5/1998 | Swift et al. | |
| 5,763,395 A | 6/1998 | Blackburn et al. | |
| 5,763,409 A | 6/1998 | Bayol et al. | |
| 5,833,948 A | 11/1998 | Tournier et al. | |
| 5,929,028 A | 7/1999 | Skrabanja et al. | |
| 6,057,428 A | 5/2000 | Keyt et al. | |
| 6,110,443 A | 8/2000 | Schneider et al. | |
| 6,120,761 A | 9/2000 | Yamazaki et al. | |
| 6,238,664 B1 | 5/2001 | Hellerbrand et al. | |
| 6,277,367 B1 | 8/2001 | Yamazaki et al. | |
| 6,284,277 B1 | 9/2001 | Bouloumie et al. | |
| 6,306,832 B1 | 10/2001 | Pietras | |
| 6,306,905 B1 | 10/2001 | Kurz et al. | |
| 6,326,406 B1 | 12/2001 | De Tommaso et al. | |
| 6,358,528 B1 | 3/2002 | Grimmett et al. | |
| 6,410,511 B2 | 6/2002 | L'Italien et al. | |
| 6,803,046 B2 | 10/2004 | Metcalfe et al. | |
| 7,329,644 B2 | 2/2008 | Saviano et al. | |
| 2002/0048748 A1 | 4/2002 | Sahner | |
| 2003/0104996 A1 | 6/2003 | Li et al. | |
| 2004/0033243 A1 | 2/2004 | Metcalfe et al. | |
| 2005/0020502 A1 | 1/2005 | Metcalfe et al. | |

(Continued)

FOREIGN PATENT DOCUMENTS

| | | |
|---|---|---|
| EP | 1136068 A2 | 9/2001 |
| EP | 1197221 A1 | 4/2002 |

(Continued)

OTHER PUBLICATIONS

ANASPEC pK and PI Values of Amino Acids wayback machine Jan. 19, 2005.
ANASPEC 2017.
Dictionary definition of physiologic-pH.
Klabunde "Cardiovascular Pharmacology Concepts" Mar. 16, 2015.
Akers "Excipient-Drug Interactions in Parenteral Formulations," Journal of Pharmaceutical Sciences, (Nov. 2002), 91(11):2283-2300.
Amaral, et al., "Gallbladder Muscle Dysfunction in Patients with Chronic Acalculous Disease," Gastroenterology, (2001), 120:506-511.
Arakawa, et al., "Factors Affecting Short-Term and Long-Term Stabilities of Proteins," Adv. Drug. Deliv. Rev., (2001), 46:307-326.

(Continued)

*Primary Examiner* — Danah Al-Awadi
(74) *Attorney, Agent, or Firm* — BakerHostetler (57) ABSTRACT

Disclosed herein are solid compositions that comprise sincalide and are storage stable and which lack a buffer, and optionally, also lack a surfactant/solubilizer, wherein such compositions are storage stable. Also disclosed herein are liquid compositions that comprise sincalide, wherein such compositions are storage stable, and may lack buffer and/or surfactant/solubilizer. Also provided are methods of making and administering the solid or liquid storage stable compositions to a patient in need of, e.g., for the treatment, prevention, and/or diagnosis of gall bladder- and/or pancreatic disorders; or other diagnostic imaging.

20 Claims, 1 Drawing Sheet

(56) References Cited

U.S. PATENT DOCUMENTS

| | | | | |
|---|---|---|---|---|
| 2010/0047175 | A1* | 2/2010 | Metcalfe | A61K 47/18 424/9.1 |
| 2015/0071879 | A1 | 3/2015 | Jezek | |

FOREIGN PATENT DOCUMENTS

| | | |
|---|---|---|
| EP | 1254666 A1 | 11/2005 |
| GB | 2478849 A | 9/2011 |
| JP | H06-273415 A | 9/1994 |
| JP | 2577744 B | 2/1997 |
| JP | 5726587 B | 6/2015 |
| WO | WO 1990/012029 A1 | 10/1990 |
| WO | WO 1995/022560 A1 | 8/1995 |
| WO | WO 1998/046250 A1 | 10/1998 |
| WO | WO 1999/034822 A1 | 7/1999 |
| WO | WO 2014/165607 A2 | 10/2014 |

OTHER PUBLICATIONS

Bacarese-Hamilton, et al. "Oxidation/Reduction of Methionine Residues in CCK: A Study by Radioimmunoassay and Isocratic Reverse Phase High Pressure Liquid Chromatography," Peptides, (1985), 6:17-22.
Bacarese-Hamilton, et al. "Prevention of Cholecystokinin Oxidation During Tissue Extraction," Neuronal Cholecystokinin, Annals of the New York Academy of Sciences, vol. 448, The New York Academy of Sciences, (1985), (14 pages).
Balon, et al., "Procedure Guideline for Hepatobiliary Scintigraphy," J. Nucl. Med., (1997), 38:1654-1657.
Bracco Diagnostics.TM., Kinevac.RTM. Sincalide for Injection, package insert, Daily Med Label (1994), (3 pages) https://dailymed.nlm.nih.gov/dailymed/archives/fdaDrugInfo.cfm?archiveid=-180757.
Bull and Breese "Surface Tension of Amino Acid Solutions: A Hydrophobicity Scale of the Amino Acid Residues," Archives of Biochemistry and Biophysics, (1974), 161:665-670.
Carpenter, et al., "Freezing- and Drying-Induced Perturbations of Protein Structure and Mechanisms of Protein Protection by Stabilizing Additives," Freeze-Drying/Lyophilization of Pharmaceutical and Biological Products, Marcel Dekker, (1999), Chapters, pp. 123-160.
Chen et al., "Morphine Augmentation Increases Gallbladder Visualization in Patients Pretreated with Cholecystokinin," J. Nucl. Med., (1997), 38:644-647.
Cleland, et al. "The Development of Stable Protein Formulations: A Close Look at Protein Aggregation, Deamidation, and Oxidation," Crit. Rev. Ther. Drug Carr. Sys., (1993), 10(4):307-377.
Cleland and Langer, "Formulation and Delivery of Proteins and Peptides," ACS Symposium Series; American Chemical Society: Washington, DC, (1994), Chapter 1, pp. 1-19. Deluca and Boylan "Formulation of Small Volume Parenterals," Chapters, Pharmaceutical Dosage Forms: Parenteral Medications, vol. 1, Marcel Dekker, (1992), (79 pages).
Doty et al., "Cholecystokinin Prophylaxis of Parenteral Nutrition-Induced Gallbladder Disease," presented at Am. Fed. Clin. Res., (Feb. 7-10, 1984).
Essentials of Nuclear Medicine Science, Williams & Wilkins, (1987), (232 pages).
FDA Summary Basis of Approval Package for NDA 017697-S012 Center for Drug Evaluation and Research, (Nov. 27, 2002), (63 pages).
Fink-Bennett, "The Role of Cholecystogogues in the Evaluation of Biliary Tract Disorders," Nucl. Med. Ann., Raven Press, (1985), 107-132.
Fink-Bennett, et al., "Cholecystokinin Cholescintigraphic Findings in the Cystic Duct Syndrome," J. Nucl. Med., (1985), 26:1123-1128.
Gorman, et al., "Proton Affinities of the 20 Common .alpha.-Amino Acids," J. Am. Chem. Soc., (1992), 114:3986-3988.

Handbook of Pharmaceutical Excipients, "Polyoxyethylene Sorbitan Fatty Acid Esters," American Pharmaceutical Association, 3rd Ed. Arthur H. Kibbe, Ed. (2000), pp. 416-419.
Handbook of Pharmaceutical Excipients, "Sodium Metabisulfite," American Pharmaceutical Association, 3rd Ed. Arthur H. Kibbe, Ed. (2000), pp. 490-494.
Handbook of Pharmaceutical Excipients, "Mannitol," American Pharmaceutical Association, 3rd Ed. Arthur H. Kibbe, Ed. (2000), pp. 324-328.
Huber RC "Lyophilization of sincalide and correlation of headspace relative humidity with product stability," J. Pharm. Sci. (1978), 67(9):1239-1243.
Huttner "Determination and Occurrence of Tyrosine O-Sulfate in Proteins," Protein Acylations/Deaclylations, Tyrosine Sulfation of Proteins, Chapter 11, Academic Press, Inc., (1984)pp. 200-223.
Kinevac.RTM., Product Information, Physician's Desk Reference for Radiology and Nuclear Medicine, Litton Industries, Inc., (1977), p. 154.
Krishnamurthy, et al., "Detection, Localization, and Quantitation of Degree of Common Bile Duct Obstruction by Scintigraphy," J. Nucl. Med., (1985), 26:726-735.
Krishnamurthy, et al., "Gallbladder Ejection Fraction: A Decade of Progress and Future Promise," J. Nucl. Med., (1992), 33:542-544.
Krishnamurthy, et al., "Measurement of Gallbladder Emptying Sequentially Using a Single Dose of 99mTc-Labeled Hepatobiliary Agent," Gastroenterology, (1982), 83:773-776.
Krishnamurthy, et al., "Quantitative Biliary Dynamics: Introduction of a New Noninvasive Scintigraphic Technique," J. Nucl. Med., (1983), 24:217-223.
Krishnamurthy, et al., "The gallbladder emptying response to sequential exogenous and endogenous cholecystokinin," Nucl. Med. Comm., (1984), 5:27-33.
Levine, et al., "Oxidation of Methionine in Proteins: Roles in Antioxidant Defense and Cellular Regulation," IUBMB Life, (2000), 50:301-307.
Li et al., "Chemical Instability of Protein Pharmaceuticals: Mechanisms of Oxidation and Strategies for Stabilization," Biotech. Bioeng., (1995), 48:490-500.
Liddle "Cholecystokinin Cells," Ann. Rev. Physiol., (1997), 59:221-242.
Liddle "On the Measurement of Cholecystokinin," Editorial, Clinical Chemistry, (1998), 44(5):903-904.
Manning, et al., "Stability of Protein Pharmaceuticals," Pharmaceutical Research, (1989), 6(11):903-918.
Marseigne, et al., "Full Agonists of CCK8 Containing a Nonhydrolyzable Sulfated Tyrosine Residue," J. Med. Chem., (1989), 32:445-449.
Mattern, et al., "Formulation of Proteins in Vacuum-Dried Glasses, II. Process and Storage Stability in Sugar-Free Amino Acid Systems," Pharm. Dev. Tech., (1999), 4(2):199-208.
Mesgarzadeh, et al., "Filling, Postcholecystokinin Emptying, and Refilling of Normal Gallbladder: Effects of Two Different Doses of CCK on Refilling: Concise Communication," J. Nucl. Med., (1983), 24:666-671.
Meyers, "New Diagnostic Tests Combining Drugs and Nuclear Medicine," WJM (1994), 161:410.
Moroder and Wunsch "Gastrin and Cholecystokinin an Arduous Task for the Peptide Chemist," Natural Product Chemistry Proceedings of the First International Symposium and Pakistan-U.S. Binational Workshop, (1986), (28 pages).
Moss, et al., "New Approaches to Understanding the Etiology and Treatment of Total Parenteral Nutrition-Associated Cholestasis," Sem. Ped. Surg., (1999), 8(3):140-147.
Nema, et al., "Excipients and Their Use in Injectable Products," PDA J. Pharm. Sci. Tech., (1997), 51:166-171.
Newman, et al., "A simple technique for quantitative cholecystokinin—HIDA scanning," Brit. J. Radiol., (1983), 56:500-502.
Nguyen, "Oxidation Degradation of Protein Pharmaceuticals," ACS Symposium Series: Formulation and Delivery of Proteins and Peptides, American Chemical Society, (1994), Chapter 4, pp. 59-71.
Pickleman, et al., "The Role of Sincalide Cholescintigraphy in the Evaluation of Patients with Acalculus Gallbladder Disease," Arch. Surg., (1985), 120:693-697.

(56) References Cited

OTHER PUBLICATIONS

Pikal, "Mechanisms of Protein Stabilization During Freeze-Drying and Storage: The Relative Importance of Thermodynamic Stabilization and Glassy State Relaxation Dynamics," Freeze-Drying/Lyophilization of Pharmaceutical and Biological Products, Marcel Dekker, (1999), Chapter 6, pp. 161-198.
Powell, et al., "Compendium of Excipients for Parenteral Formulations," PDA J. Pharm. Sci. Tech., (1998), 52:238-311.
Rational Design of Stable Protein Formulations Theory and Practice, Pharmaceutical Biotechnology, vol. 13, Chapters 1-3, Kluwer Academic/Plenum Publishers, (2002), (101 pages).
Rational Design of Stable Protein Formulations Theory and Practice, Pharmaceutical Biotechnology, vol. 13, Chapters 4-8, Kluwer Academic/Plenum Publishers, (2002), (121 pages).
Sargent, "Cholecystokinetic cholecystography: efficacy and tolerance study of sincalide" Am. J. Roentgenol., (1976), 127: 267-271.
Sawaf, et al., "Gastroesophageal Reflux Demonstrated by Hepatobiliary Imaging in Scleroderma," J. Nucl. Med., (1987), 28:387-389.
Shah, et al., "The Effects of Various Excipients on the Unfolding of Basic Fibroblast Growth Factor," PDA J. Pharm. Sci. Tech., (1998), 52:209-214.
Shechter, et al., "Selective Oxidation of Methionine Residues in Proteins," Biochemistry, (1975), 14(20):4497-4503.
Sincalide, Product Information, Physician's Desk Reference, PDR Generics, Second Edition, Medical Economics Company at Montvale, (1996), pp. 2754-2755.
Sincalide for Injection, U.S. Pharmacopeia & National Formulary 24, The National Formulary 19, The United States Pharmacopeial Convention, Inc., (1999), 1522-1523.
Sitzmann, et al., "Cholecystokinin Prevents Parenteral Nutrition-Induced Biliary Sludge in Humans," Surgery, Gyn. Obst., (1990), 170:25-31.
Strickley, "Parenteral Formulations of Small Molecules Therapeutics Marketed in the United States (1999)—Part I," PDA J. Pharm. Sci. Tech., (1999), 53:324-349.
Strickley, "Parenteral Formulations of Small Molecules Therapeutics Marketed in the United States (1999)—Part II," PDA J. Pharm. Sci. Tech., (2000), 54:69-96.
Strickley, "Parenteral Formulations of Small Molecules Therapeutics Marketed in the United States (1999)—Part III," PDA J. Pharm. Sci. Tech., (2000), 54:152-169.
Teitelbaum, "Parenteral nutrition-associated cholestasis," Curr. Opin. Ped., (1997), 9:270-275.
Teitelbaum, et al., "Parenteral Nutrition-Associated Cholestasis," Sem. Ped. Surg., (2001), 10:72-80.
Teitelbaum, et al., "Treatment of Parenteral Nutrition-Associated Cholestasis with Cholecystokinin-Octapeptide," J. Ped. Surg., (1995), 30:1082-1085.
Tien, et al., "Peroxynitrite-mediated modification of proteins at physiological carbon dioxide concentration: pH dependence of carbonyl formation, tyrosine nitration, and methionine oxidation," Proc. Natl. Acad. Sci. USA, (1999), 96:7809-7814.
Uffelman, "Unexpected Shortfalls of Two Nuclear Medicine Pharmaceuticals," Public Affairs Update, The Journal of Nuclear Medicine, (2001), 42(10):14N-19N.
Vyas, et al., "Estimation of Gallbladder Ejection Fraction Utilizing Cholecystokinin-Stimulated Magnetic Resonance Cholangiography and Comparison with Hepatobiliary Scintigraphy," JMRI, (2002), 15:75-81.
Wang, "Parenteral Products of Peptides and Proteins," Chapter 7, Pharmaceutical Dosage Forms: Parenteral Medications vol. 1, Marcel Dekker, Inc., (1992), 283-319.
Wang and Hanson, "Parenteral Formulations of Proteins and Peptides: Stability and Stabilizers," J. Paren. Sci. Tech., (1988), 42:S4-S26.
Wang et al., "Review of Excipients and pHs for Parenteral Products Used in the United States," PDA J. Pharm. Sci. Tech., (1980), 34:452-462.
Wang, "Instability, Stabilization and Formulation of Liquid Protein Pharmaceuticals," Int'l. J. Pharm., (1999), 185:129-188.
Wang, et al., "Lyophilization and Development of Solid Protein Particles," Int. J. Pharm., (2000), 203:1-60.
Waterman et al., "Stabilization of Pharmaceuticals to Oxidative Degradation," Pharm. Dev. Tech., (2002), 7:1-32.
Wunsch, "Peptide Factors as Pharmaceuticals: Criteria for Application," Biopolymers, (1983), 22:493-505.
Yagami, et al., "Stabilization of a tyrosine O-sulfate residue by a cationic functional group: formation of a conjugate acid-base pair," J. Peptide Res., (2000), 56:239-249.
Yoshioka and Stella "Stability of Peptide and Protein Pharmaceuticals," Chapter 5: Stability of Drugs and Dosage Forms, Kluwer Academic Publishers, (2002), pp. 187-203.
Zhou and Po, "Peptide and Protein Drugs: I. Therapeutic Applications, Absorption and Parenteral Administration," Int'l. J. Pharm., (1991), 75:97-115.
Ziessman, et al., "Calculation of a Gallbladder Ejection Fraction: Advantage of Continuous Sincalide Infusion over the Three-Minute Infusion Method," J. Nucl. Med., (1992), 33:537-541.
Ziessman, "Cholecystokinin Cholescintigraphy: Victim of Its Own Success?" J. Nucl. Med., (1999), 40(12):2038-2042.
Invitation to Pay Additional Fees with respect to PCT/2018/048004 dated Oct. 3, 2018.
International Search Report and Written Opinion with respect to PCT/2018/048004 dated Dec. 11, 2018.
Beynon and Easterby, "Buffer Solutions" Oxford University Press, Walton Street, Oxford OX2 6DP, copyright 1996, 25 pages.
Stoll and Blanchard, "[4] Buffers: Principles and Practice," General Methods for Handling Proteins and Enzymes, Methods in Enzymology, 1990, 182:24-38.
Amended Joint Claim Construction and Prehearing Statement, Filed in Case No. 3:17-cv-13151-PGS-TJB, Document 46, Filed Dec. 26, 2018, 46 pages.
Opening Claim Construction Brief of MAIA Pharmaceuticals, Inc., Filed in Case No. 3:17-cv-13151-PGS-TJB, Document 53, Filed Feb. 19, 2019, 200 pages.
Plaintiff Bracco Diagnostics Inc.'s Opening Markman Claim Construction Submission Pursuant to Local Patent Rule 4.5(a), Filed in Case No. 3:17-cv-13151-PGS-TJB, Document 54, Filed Feb. 19, 2019, 1687 pages (uploaded as pp. 1-150, pp. 151-250, pp. 251-325, pp. 326-375, pp. 376-450, pp. 451-550, pp. 551-600, pp. 601-750, pp. 751-900, pp. 901-1100, pp. 1101-1200, pp. 1201-1300, pp. 1301-1450, pp. 1451-1600, and pp. 1601-1687).
Responsive Claim Construction Brief of Maia Pharmaceuticals, Inc., Filed in Case No. 3:17-cv-13151-PGS-TJB, Document 61, Filed Apr. 16, 2019, 43 pages.
Plaintiff Bracco Diagnostics Inc.'s Responding Markman Claim Construction Submission Pursuant to Local Patent Rule 4.5(c), Filed in Case No. 3:17-cv-13151-PGS-TJB, Document 62, Filed Apr. 16, 2019, 43 pages (uploaded as pp. 1-200, pp. 201-350, pp. 351-500, and pp. 501-799).
Declaration Christian Schoneich, Ph.D., in Support of Petition for Inter Partes Review of U.S. Pat. No. 6,803,046, 88 pages.
Forrest_Testimony, Bracco v. Maia, Maia v. Bracco, Case3:17-cv-13151-PGS-TJB, Document 62-12, 317 pages.
Klibanov_Testimony, Bracco v. Maia, Maia v. Bracco, Case 3:17-cv-13151-PGS-TJB, Document 62-6, 263 pages.
Declaration of Laird Forrest, Ph.D., Case 3:17-cv-13151-PGS-TJB, Document 54-1, 117 pages.
Declaration of Alexander M. Klibanov in Support of Defendant Maia Pharmaceuticals, Inc.'s Opening Claim Construction Brief, Case 3:17-cv-13151-PGS-TJB, Document 53-1, 84 pages.
Responsive Declaration of Professor Alexander M. Klibanov in Support of Defendant Maia Pharmaceuticals, Inc.'s Responsive Claim Construction Brief, Case 3:17-cv-13151-PGS-TJB, Document 61-1, 14 pages.
Second Declaration of Laird Forrest, Ph.D., Case 3:17-cv-13151-PGS-TJB, Document 62-1, 45 pages.
Information Disclosure Statement Transmittal Letter with respect to U.S. Appl. No. 15/958,854 submitted on Aug. 19, 2019.
Markman Ruling, Memorandum and Order, Bracco Diagnostics, Inc. Plaintiff, v. Maia Pharmaceuticals, Inc. Defendants, Case 3:17-cv-13151-PGS-TJB Document 85 Filed Oct. 3, 2019, 21 pages.

(56) References Cited

OTHER PUBLICATIONS

Zuzel, et al., "Assessment of the role of "enkephalinase" in cholecystokinin inactivation" Neuroscience, vol. 15. No. 1, 1985, pp. 149-158.

Rose et al., "Protection by serine peptidase inhibitors of endogenous cholecystokinin released from brain slices" Neuroscience, vol. 29, No. 3, 1989, pp. 583-594.

Extended Search Report issued in European Application No. 18848230. 1, dated Mar. 5, 2021.

Balon et al.; "Society of Nuclear Medicine Procedure Guideline for Hepatobiliary Scintigraphy"; Society of Nuclear Medicine Procedure Guidelines Manual; Version 3.0; Mar. 2003; p. 59-64.

* cited by examiner

STORAGE STABLE SINCALIDE FORMULATIONS

CROSS-REFERENCE TO RELATED APPLICATIONS

This application is a divisional application of U.S. patent application Ser. No. 15/958,854, filed Apr. 20, 2018 (now allowed), which claims benefit under 35 U.S.C. § 119(e) of U.S. Provisional Patent Application No. 62/550,484, filed Aug. 25, 2017, and entitled "Storage Stable Sincalide Formulations", all of which are herein incorporated by reference in their entirety.

TECHNICAL FIELD

Disclosed herein are storage stable solid compositions of sincalide that are substantially free of buffers (and optionally surfactants/solubilizers), methods of making and using the compositions, and kits comprising the compositions. Also disclosed herein are storage stable liquid compositions of sincalide, methods of making and using the compositions, and kits comprising the liquid compositions. Such liquid compositions may also be substantially free of buffers (and optionally surfactants/solubilizers).

BACKGROUND OF THE INVENTION

Sincalide is a cholecystopancreatic-gastrointestinal hormone peptide for parenteral administration. The active pharmaceutical ingredient, 1-De(5-oxo-L-glutamine-5-L-proline)-2-de-L-methioninecaerulein or "sincalide" (CAS #25126-32-3), is a synthetically prepared C-terminal octapeptide of cholecystokinin (CCK-8), with the following amino acid sequence: Asp-Tyr($SO_3H$)-Met-Gly-Trp-Met-Asp-Phe-$NH_2$.

Sincalide (KINEVAC® Sincalide for Injection) was first approved by Food and Drug Administration (FDA) in 1976, and was supplied as a sterile, nonpyrogenic, lyophilized white powder in containing nominally 5 µg sincalide, 45 mg sodium chloride as a bulking/tonicity agent, and sodium hydroxide or hydrochloric acid to adjust the pH to pH 5.5-6.5. The 5-mL Type I glass vial was sealed under a nitrogen headspace with a relative humidity (RH) of less than 30% in the headspace of the vial (Huber R C (1978) J. Pharm. Sci. 67(9): 1239-1243). This two-ingredient formulation was approved with an 18-month shelf life when stored at −20° C. or below (U.S. Pat. No. 3,937,819; FDA Summary Basis of Approval for NDA 017697). The recommended storage temperature is reported to be −4° C. elsewhere (Sargent N E (1976) Am. J. Roentgenol. 127: 267-271). This two-ingredient formulation (Sincalide for Injection) was incorporated into the U.S. Pharmacopeia, USP 24, NF 19, Jan. 1, 2000, but the monograph remained unenforceable and was withdrawn in 2011.

Various drawbacks in the manufacturing and analysis of the two-ingredient formulation of sincalide have been reported (U.S. Pat. No. 6,803,046). For example, the potency of the two-ingredient formulation was analyzed using a guinea pig gallbladder contraction bioassay, with a wide acceptance range of 80-125%. This bioassay was reportedly unable to distinguish between the bioactivity of sincalide and the bioactivity of sincalide degradants. Accordingly, a 20% overage of sincalide was required in previous sincalide formulations to compensate for the limitations of the bioassay (U.S. Pat. No. 6,803,046, supra). The U.S. Pharmacopeia has since removed the Sincalide for Injection monograph from the USP since it deemed the complex functional bioassay not suitable for use as a public standard and its attempts to replace the functional bioassay with a quantitative chemical assay were not successful.

Another lyophilized formulation of Sincalide (KINEVAC®) was approved in 2002, and contained the following ingredients: 170 mg mannitol as a bulking agent/tonicity adjuster; 30 mg of lysine, 15 mg of arginine, and 4 mg of methionine as stabilizers; 2 mg of pentetic acid as a chelator; 0.04 mg of sodium metabisulfite as a stabilizer/antioxidant; 0.005 mg of polysorbate (Tween) 20 as a surfactant/solubilizer; 9 mg potassium phosphate dibasic as a buffer; and hydrochloric acid and/or sodium hydroxide to adjust the pH to 6.0 to 8.0 (Daily Med "Label: Kinevac—sincalide injection, powder, lyophilized, for solution" NIH: U.S. National Library of Medicine, last updated Jul. 13, 2015; U.S. Pat. No. 6,803, 046, supra). The purity of this formulation was assessed by a sincalide-specific assay such as high-performance liquid chromatography (HPLC).

The current formulation of KINEVAC® has been in recurrent shortages: it was first listed in the FDA Drug Shortages database from June 2013 to December 2015, and is currently on the FDA shortage list again since Mar. 1, 2017. Additionally, the current formulation of KINEVAC® appears to have issues with stability, as in January 2015, FDA approved a request to have KINEVAC's® shelf-life reduced from 24 months to 15 months when stored at 25° C.

There is thus need for additional solid formulations of sincalide with pharmaceutically acceptable stability profiles.

Additionally, ready-to-use (e.g., ready-to-dilute) formulations for sincalide are currently not available. Lyophilized products must be reconstituted in the appropriate diluent with the appropriate volume of the diluent prior to administration to the patient. In some cases, the reconstituted solution may further need to be diluted prior to use. Additional drug preparation steps such as reconstitution and dilution can result in errors in the drug preparation process (wrong drug-preparation error as defined by ASHP Guidelines on Preventing Medication Errors in Hospitals). Medication errors compromise patients' health and safety, their confidence in the health care system, and increase healthcare costs. This ASHP guideline thus recommends the use of medications in ready-to-administer forms whenever possible.

There is thus need for ready-to-use, including ready-to-dilute, liquid formulations of sincalide that are storage stable and eliminate or reduce the potential for drug preparation errors.

SUMMARY OF THE INVENTION

Figure 1:
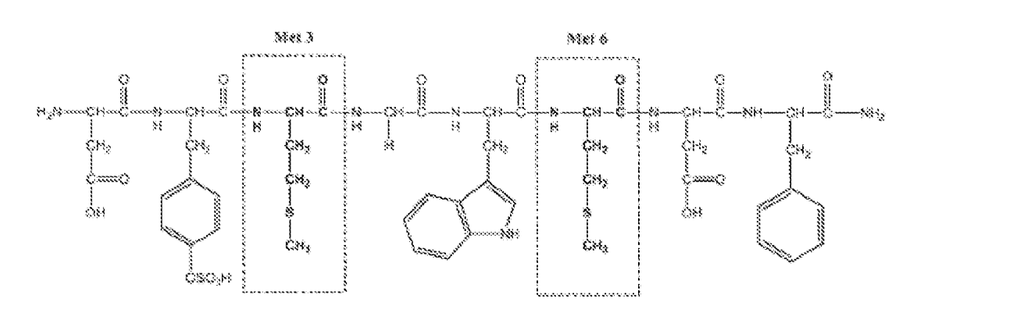
FIG. 1 is the chemical structure of sincalide.

Described herein are solid (lyophilized) or liquid (aqueous ready-to-use (e.g., ready-to-dilute) formulations, reconstituted formulations, etc.) of sincalide that are surprisingly stable in storage. See, e.g., Tables 3, 5-8. Such stability is unexpected in light of the stability profile of previous sincalide formulations that demonstrated a shelf-life of less than 18 months in long term storage (25° C.) conditions in lyophilized forms. Such unexpected findings are seen despite solid compositions herein lacking a buffer, or lacking a buffer and surfactant/solubilizer.

More surprising is the demonstration herein that an aqueous solution of sincalide may have a shelf-life of at least 3 months, 6 months, or 12 months in long term storage (2°-8° C.) conditions. Such aqueous sincalide compositions may also lack a buffer or also lack both a buffer and surfactant/solubilizer.

Compositions comprising the storage stable formulations, methods of making the compositions, kits comprising the compositions (e.g., in appropriate vials, and optionally a fluid portion (e.g., Water for Injection) for reconstituting the lyophilized compositions described herein), and use of the compositions, e.g., in therapeutic, diagnostic, and/or imaging methods, are provided.

Described herein are compositions comprising sincalide, wherein the compositions have an unexpected shelf-life. The sincalide compositions described herein may be in the form of a lyophilized powder, e.g., may be solid, for example, one which is packaged under a vacuum or partial vacuum.

In some embodiments, described herein is a solid (lyophilized) composition comprising sincalide, wherein the shelf-life of the solid (lyophilized) composition is at least 18 months, or, for example, at least 24 months when stored at 25° C. and 60% relative humidity, e.g., wherein after 18 months (or 24 months) of storage at 25° C. and 60% relative humidity, and as measured by HPLC, the composition comprises
  (a) less than 5% total impurities,
  (b) retains at least 90% of active sincalide
  (c) less than 2% of any individual impurity, and
  (d) any combination of (a)-(c),
and wherein the solid (lyophilized) composition does not comprise dibasic potassium phosphate.

In some embodiments, described herein is a solid (lyophilized) composition comprising sincalide, wherein the shelf-life of the solid (lyophilized) composition is at least 15 months when stored at 25° C. and 60% relative humidity, e.g., wherein after 15 months of storage at 25° C. and 60% relative humidity, and as measured by HPLC, the composition comprises
  (a) less than 5% total impurities,
  (b) retains at least 90% of active sincalide
  (c) less than 2% of any individual impurity, and
  (d) any combination of (a)-(c),
and wherein the solid (lyophilized) composition does not comprise dibasic potassium phosphate.

In some further embodiments, described herein is a solid (lyophilized) composition comprising sincalide, wherein the shelf-life of the solid (lyophilized) composition is at least 12 months when stored at 25° C. and 60% relative humidity, e.g., wherein after 12 months of storage at 25° C. and 60% relative humidity, and as measured by HPLC, the composition comprises
  (a) less than 4% total impurities,
  (b) retains at least 90% of active sincalide
  (c) less than 1.5% of any individual impurity, and
  (d) any combination of (a)-(c),
and wherein the solid (lyophilized) composition does not comprise dibasic potassium phosphate.

In some other further embodiments, described herein is a solid (lyophilized) composition comprising sincalide, wherein the shelf-life of the lyophilized composition is at least 9 months when stored at 25° C. and 60% relative humidity, e.g., wherein after 9 months of storage at 25° C. and 60% relative humidity, and as measured by HPLC, the composition comprises
  (a) less 2.5% total impurities,
  (b) retains at least 95% of active sincalide
  (c) less than 1.5% of any individual impurity, and
  (d) any combination of (a)-(c),
and wherein the solid (lyophilized) composition does not comprise dibasic potassium phosphate.

In some embodiments, the solid (lyophilized) composition does not comprise a phosphate buffer. In some embodiments, the solid (lyophilized) composition does not comprise any buffers. In some further embodiments, the solid (lyophilized) compositions do not comprise buffer and also do not comprise surfactant/solubilizer.

The solid compositions described herein include, for example, pharmaceutical sincalide compositions including: a therapeutically effective amount of sincalide; 1 to 4 mg pentetic acid; 15 to 45 mg arginine hydrochloride; 2 to 8 mg methionine; 7.5 to 30 mg lysine hydrochloride; 0.02 to 1 mg sodium metabisulfite; 85 to 340 mg mannitol; and have a pH from 6.5 to 7.5, wherein the composition does not contain a buffer having a pKa within one unit of the pH, and wherein the composition is storage stable. Such compositions can be a lyophilized powder, and can be packaged under a vacuum.

Compositions described herein may be liquid, e.g., in the form of a ready-to-use aqueous sincalide solution which exhibits storage stability. For example, the aqueous sincalide solutions described herein, after being stored for 6 months at 2°-8° C. contain less than 5% total impurities, more than 90% of active sincalide, and less than 2% of any individual impurity.

Also described herein is a liquid (e.g., an aqueous ready-to-use composition, a reconstituted lyophilized composition, etc.) comprising sincalide, wherein the shelf-life of the aqueous composition is at least 18 months when stored at 2°-8° C., e.g., wherein after 18 months of storage at 2°-8° C., and as measured by HPLC, the composition comprises
  (a) less than 5% total impurities,
  (b) at least 90% of active sincalide
  (c) less than 2% of any individual impurity, and
  (d) any combination of (a)-(c).

Also described herein is a liquid (e.g., an aqueous ready-to-use composition, a reconstituted lyophilized composition, etc.) comprising sincalide, wherein the shelf-life of the aqueous composition is at least 18 months when stored at 2°-8° C., e.g., wherein after 15 months of storage at 2°-8° C., and as measured by HPLC, the composition comprises
  (a) less than 5% total impurities,
  (b) at least 90% of active sincalide
  (c) less than 2% of any individual impurity, and
  (d) any combination of (a)-(c).

Also described herein a liquid (e.g., an aqueous ready-to-use composition, a reconstituted lyophilized composition, etc.) composition comprising sincalide, wherein the shelf-life of the aqueous composition is at least 12 months when stored at 2°-8° C., e.g., wherein after 12 months of storage at 2°-8° C., and as measured by HPLC, the composition comprises
  (a) less than 5% total impurities,
  (b) at least 90% of active sincalide
  (c) less than 2% of any individual impurity, and
  (d) any combination of (a)-(c).

Also described herein is a liquid (e.g., an aqueous ready-to-use composition, a reconstituted lyophilized composition, etc.) composition comprising sincalide, wherein the shelf-life of the aqueous composition is at least 6 months when stored at 25° C./65% relative humidity, e.g., wherein after 6 months of storage at 2°-8° C., and as measured by HPLC, the composition comprises
  (a) less than 5% total impurities,
  (b) at least 90% of active sincalide
  (c) less than 2% of any individual impurity, and
  (d) any combination of (a)-(c).

Also described herein is a liquid (e.g., an aqueous ready-to-use composition, a reconstituted lyophilized composition, etc.) composition comprising sincalide, wherein the shelf-life of the aqueous composition is at least 3 months when stored at 25° C./65% relative humidity, e.g., wherein after 3 months of storage at 2°-8° C., and as measured by HPLC, the composition comprises
  (a) less than 5% total impurities,
  (b) at least 90% of active sincalide
  (c) less than 2% of any individual impurity, and
  (d) any combination of (a)-(c).

In some embodiments, the liquid composition does not comprise dibasic potassium phosphate. In some embodiments, the liquid composition does not comprise a phosphate buffer. In some embodiments, the liquid composition does not comprise any buffers. In some embodiments, the liquid compositions do not comprise any buffers and do not comprise any surfactant/solubilizer.

Other embodiments of such compositions can be ready-to-use aqueous solutions, for example, comprising: a therapeutically effective amount of sincalide; 0.4 to 5 mg/mL pentetic acid; 6 to 30 mg/mL arginine hydrochloride; 0.8 to 5 mg/mL methionine; 3 to 15 mg/mL lysine hydrochloride; 0.008 to 1 mg/mL sodium metabisulfite; and 34 to 170 mg/mL mannitol, exhibiting storage stability, such that the compositions, for example, stored at 2°-8° C. for 6 months contain less than 5% total impurities, more than 90% active sincalide, and less than 2% of any individual impurity. Such aqueous compositions may lack a buffer, or optionally may additionally lack a surfactant/solubilizer The solid or liquid sincalide compositions described herein may comprise a stabilizer and/or a bulking agent/tonicity adjuster. In some embodiments, the stabilizer is selected from the group consisting of pentetic acid, arginine hydrochloride, L-methionine, L-lysine hydrochloride, sodium metabisulfite, and a combination thereof. In some embodiments, the bulking agent/tonicity adjuster comprises mannitol.

In particular embodiments, compositions described herein may comprise sincalide, wherein the composition does not contain a buffer (e.g., does not contain a phosphate buffer, such as dibasic potassium phosphate), and wherein the composition is stable in storage. Sincalide compositions described herein may further comprise a stabilizer (e.g., pentetic acid, arginine hydrochloride, L-methionine, L-lysine hydrochloride, sodium metabisulfite, or combinations thereof) and/or a bulking agent/tonicity adjuster (e.g., mannitol). The sincalide compositions described herein may also not contain a surfactant/solubilizer (e.g., polysorbate 20 or polysorbate 80). Some particular sincalide compositions described herein contain neither dibasic potassium phosphate, nor polysorbate 20.

The sincalide compositions described herein may contain chelators (e.g. pentetic acid), stabilizers (e.g., combinations of L-arginine hydrochloride, L-methionine, L-lysine hydrochloride, and sodium metabisulfite), and bulking agents/tonicity adjusters (e.g., mannitol), buffers (e.g., dibasic potassium phosphate), and surfactants/solubilizers (e.g., polysorbate 20).

The description also includes methods of making storage stable sincalide compositions by mixing: a therapeutically effective amount of sincalide; and an excipient, wherein the excipient consists essentially of: at least one stabilizer; at least one bulking agent/tonicity adjuster; at least one chelator, or any combination of these (e.g., L-arginine hydrochloride, L-methionine, L-lysine hydrochloride, sodium metabisulfite, mannitol, and pentetic acid), and water, wherein the composition has a pH from 6.5 to 7.5, and the storage stable solid sincalide composition does not contain a buffer having a pKa within one unit of the pH, or neither contains a buffer nor a surfactant/solubilizer. Such methods of making storage stable solid sincalide compositions can also include lyophilizing the mixture of sincalide, excipients and water, e.g., under a vacuum.

Aqueous sincalide compositions can also be made by mixing: a therapeutically effective amount of sincalide; and excipients, wherein the excipients comprise: at least one stabilizer; at least one bulking agent/tonicity adjuster; at least one chelator, or any combination of these (e.g., L-arginine hydrochloride, L-methionine, L-lysine hydrochloride, sodium metabisulfite, mannitol, and pentetic acid), and water, wherein the composition has a pH from 6.5 to 7.5. These storage stable aqueous sincalide compositions also may lack a buffer having a pKa within one unit of the pH, or lack both a buffer and a surfactant/solubilizer.

The description also includes methods for the treatment, prevention, and/or diagnosis of gall bladder- and/or pancreatic disorders; or other diagnostic imaging a patient in need thereof by administering to the patient pharmaceutical sincalide compositions described herein (containing excipients, for example, L-arginine hydrochloride, L-methionine, L-lysine hydrochloride, sodium metabisulfite, mannitol, and pentetic acid).

Also described herein are kits comprising the described compositions optionally also including a fluid component.

DETAILED DESCRIPTION

Described herein are solid formulations of sincalide that are surprisingly as stable and/or more stable than KINEVAC® even though the compositions lack a buffer (e.g., lack dibasic potassium phosphate, lack any phosphate buffer, and/or lack any buffer), and optionally, lack both a buffer and a surfactant/solubilizer. In addition, described here are liquid formulations of sincalide which display storage stability, and optionally lack a buffer or lack both a buffer and surfactant/solubilizer. Since sincalide may be administered as an intravenous bolus or by intravenous infusion or by intramuscular administration, there is a need for aqueous liquid formulations of sincalide that are storage stable either under USP controlled room temperature or refrigerated conditions.

In contrast to the marketed lyophilized KINEVAC® sincalide formulation (for which the ingredients are dissolved in water, sterilized by filtration, filled into vials, and subjected to a lyophilization process in order to remove the water, and thus require KINEVAC® reconstitution in 5 mL of Sterile Water for Injection and/or dilution in 30 or 100 mL of 0.90 Sodium Chloride Injection prior to use), the use of aqueous ready-to-dilute or ready-to-use formulations and storage stable compositions described herein reduces the number of errors introduced in preparation of the drug product.

"Sincalide" includes the synthetically-prepared C-terminal octapeptide of cholecystokinin (CCK-8), with the amino acid sequence: Asp-Tyr($SO_3H$)-Met-Gly-Trp-Met-Asp-Phe-$NH_2$, as well as derivatives thereof which have been optimized or modified (to improve stability, potency, pharmacokinetics, etc.), but retain the biological activity of the original octapeptide. For example, monomeric or multimeric forms of the octapeptide, portions of the octapeptide, and/or or octapeptides in which the methionine and/or aspartic acid residues are included within the term "sincalide" so long as the forms, portions and/or derivatives thereof retain the biological activity of CCK8.

"Ready-to-dilute" and/or "ready-to-use" refers to a sterile aqueous (liquid) injectable composition that has not been reconstituted from a lyophilized composition. In some embodiments (e.g., ready-to-dilute), the "ready-to-use" formulation can be further diluted in an appropriate diluent, e.g., a pharmaceutically acceptable carrier, such as but not limited to Sterile Water for Injection, 0.9% Sodium Chloride Injection, or 5% Dextrose in Water, to a lower sincalide concentration for administration.

Solid Compositions

Described herein are solid compositions comprising sincalide, wherein the compositions lack a buffer, or lack both a buffer and a surfactant/solubilizer, and wherein the compositions are storage stable. Although the solid compositions described herein comprise sincalide, are storage stable, and lack a buffer, and optionally lack a surfactant/solubilizer, the compositions may otherwise include a variety of excipients that are not a buffer (and optionally not a surfactant/solubilizer) including, antioxidants, bulking agents/tonicity adjusters, chelating agents, complexing agents, crosslinking agents, co-solvents, osmolality adjustors, stabilizers, pH adjustors, lyoprotectants/cryoprotectants, air/liquid and/or ice-liquid interface protectants (protectants against surface induced denaturation), freeze-thaw protectants, protectants against protein/peptide denaturation, protectants for rehydration, and wetting agents. In some embodiments, the solid compositions described herein comprise sincalide, are storage stable, lack a buffer and also optionally lack a surfactant/solubilizer, and further comprise excipients that perform the functions of at least: (i) a stabilizer, (ii) a bulking agent/tonicity adjuster, and/or (iii) a chelator. Typically, each of these functions is performed by a different excipient. However, in some embodiments of the invention a single excipient may perform more than one function. For example, a single excipient may be multi-functional, e.g. amino acids may function as bulking agents and/or stabilizers and other excipients may function, for example, as both a stabilizer and a chelator or as both a bulking agent and a tonicity adjuster. Alternatively, multiple excipients serving the same function may be used. For example, the formulation may contain one or more excipients that function as, for example, a stabilizer. "Excipient" as used herein does not include any ingredient having a pKa within one unit of the pH of a solid composition disclosed herein prior to lyophilization, which is generally between 6.5 to 7.5.

Liquid Compositions

Described herein are storage stable liquid compositions comprising sincalide. The liquid compositions may optionally lack a buffer, and may further optionally lack both a buffer and a surfactant/solubilizer. The compositions may include a variety of excipients including, antioxidants, bulking agents/tonicity adjusters, chelating agents, complexing agents, crosslinking agents, co-solvents, osmolality adjustors, stabilizers, pH adjustors, lyoprotectants/cryoprotectants, air/liquid and/or ice-liquid interface protectants (protectants against surface induced denaturation), freeze-thaw protectants, protectants against protein/peptide denaturation, protectants for rehydration, and wetting agents. In some embodiments, the liquid compositions described herein comprise sincalide, are storage stable, and comprise excipients that perform the functions of at least: (i) a stabilizer, (ii) a bulking agent/tonicity adjuster, and/or (iii) a chelator (such liquid sincalide compositions may lack a buffer and optionally may also lack both a buffer and a surfactant/solubilizer). Typically, each of these functions is performed by a different excipient. However, in some embodiments of the invention a single excipient may perform more than one function. For example, a single excipient may be multi-functional, e.g. amino acids may function as bulking agents and/or stabilizers and other excipients may function, for example, as both a stabilizer and a chelator or as both a bulking agent and a tonicity adjuster. Alternatively, multiple excipients serving the same function may be used. For example, the formulation may contain one or more excipients that function as, for example, a stabilizer. In embodiments described herein, wherein the liquid sincalide formulations lack a buffer, an excipient as used herein does not include any ingredient having a pKa within one unit of the pH of a liquid composition disclosed herein, which is generally between 6.5 to 7.5.

Buffers

The solid sincalide formulations as described herein lack, and the liquid sincalide formulations as described herein optionally lack, buffers. Buffers are generally employed to stabilize the pH of a given formulation. In particular embodiments, a buffer has a pKa within one unit of a desired formulation pH. In some embodiments, a composition as described herein comprises sincalide, is storage stable, and lacks a buffer having a pKa within one unit of the pH of the composition. A buffer may be phosphoric acid, phosphate (e.g., monobasic or dibasic sodium phosphate, monobasic or dibasic potassium phosphate, etc.), citric acid, citrate (e.g., sodium citrate, etc.), sulfosalicylate, acetic acid, acetate (e.g., potassium acetate, sodium acetate, etc.), methyl boronic acid, boronate, disodium succinate hexahydrate, lactic acid, lactate (e.g., sodium lactate, etc.), maleic acid, maleate, potassium chloride, benzoic acid, sodium benzoate, carbonic acid, carbonate (e.g., sodium carbonate, etc.), bicarbonate (e.g., sodium bicarbonate, etc.), boric acid, sodium borate, sodium chloride, succinic acid, succinate (e.g., sodium succinate), tartaric acid, tartrate (e.g., sodium tartrate, etc.), tris-(hydroxymethyl)aminomethane, biological buffers (such as N-2-hydroxyethylpiperazine,N'-2-ethanesulfonic acid (HEPES), CHAPS and other "Good's" buffers), or any combination thereof. In some embodiments, a composition as described herein comprises sincalide, is storage stable, and lacks a buffer, wherein the buffer is a phosphate buffer. In some embodiments, a composition as described herein comprises sincalide, is storage stable, and lacks a buffer, wherein the buffer is dibasic potassium phosphate. Despite lacking a buffer, a sincalide composition described herein preferably has a pH from 6.0 to 8.0, e.g., as a ready-to-use or ready-to-dilute aqueous formulation or, for the lyophilized forms described herein, as an aqueous composition just prior to lyophilization and/or just after reconstitution of a lyophilized formulation. In some embodiments, despite lacking a buffer, compositions described herein preferably have a pH from 6.5 to 7.5, e.g., as a solid formulation prior to lyophilization or after reconstitution from the solid phase, or as ready-to-use or ready-to-dilute aqueous formulations.

Surfactants/Solubilizers

A surfactant/solubilizer is used to generally reduce the interfacial tension or aid in solubilization thus preventing or reducing denaturation and/or degradation at air/liquid or liquid/solid interfaces of a peptide in solution. As described herein, the compositions comprise sincalide, lack a buffer in solid form or optionally lack a buffer in liquid form, and optionally also lack a surfactant/solubilizer. Accordingly, as described herein, the compositions may comprise sincalide and a surfactant/solubilizer, and lack a buffer. In some embodiments, a composition described herein comprises sincalide and optionally a surfactant/solubilizer, is storage stable, and lacks a buffer, e.g., dibasic potassium phosphate. A surfactant/solubilizer as described herein may be selected from the group consisting of free fatty acids; esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids; glycerides or soya-oil and sucrose; sodium caprolate; ammonium sulfate; sodium dodecyl sulfate (SDS); Triton-100 and anionic surfactants containing alkyl, aryl or heterocyclic structures; and any combination thereof. In some embodiments, a composition as described herein comprises sincalide, is storage stable, lacks a buffer (e.g., dibasic potassium phosphate) and comprises or lacks a surfactant/solubilizer selected from the group consisting of a pluonic (e.g., Lutrol F68, Lutrol F127), Poloxamers, SDS, Triton-100, polysorbates such as TWEEN® 20 and TWEEN® 80, propylene glycol, PEG and similar compounds, Brij58 (polyoxyethylene 20 cetyl ether), cremophor EL, cetyl trimethylammonium bromide (CTAB), dimethylacetamide (DMA), NP-40 (Nonidet P-40), and N-methyl-2-pyrrolidone (Pharmasolve), anionic surfactants containing alkyl, aryl or heterocyclic structures, and cyclodextrins. In some embodiments, a composition as described herein comprises sincalide, is storage stable, lacks a buffer (e.g., dibasic potassium phosphate) and comprises or lacks a surfactant/solubilizer, wherein the surfactant/solubilizer is a polysorbate. In some embodiments, a solid composition as described herein comprises sincalide, is storage stable, lacks a buffer (e.g., dibasic potassium phosphate), and lacks or comprises a surfactant/solubilizer, wherein the surfactant/solubilizer is a polysorbate 20.

Stabilizers/Chelators

In some embodiments, a composition as described herein comprises sincalide and a stabilizer, wherein the composition does not contain (i.e., lacks) a buffer (e.g., dibasic potassium phosphate) and optionally also does not contain a surfactant/solubilizer (e.g., polysorbate 20), and wherein the composition is storage stable. A wide variety of antioxidants or reducing agents can be used as stabilizers, including but not limited to, acetylcysteine, cysteine, ascorbic acid, benzyl alcohol, citric acid, pentetic acid or diethylenetriamine pentaacetic acid (DTPA), propyl gallate, methylparaben, sulfoxylate, propylparaben, edetic acid or ethylenediaminetetraacetic acid (EDTA), disodium EDTA dihydrate, dithiothreitol, glutathione, monothioglycerol, potassium metabisulfite, sodium formaldehyde sulfoxylate, sodium sulfite, sodium succinate, sodium metabisulfite, stannous chloride, thioacetic acid, thiodiglycerol, thioethanolamine, thioglycolic acid, 2-aminoethanethiol (cysteamine), butylated hydroxyanisole (BHT), and sodium sulfate and derivatives thereof, including salts and sulfurous acid salts. Sodium metabisulfite is a preferred antioxidant stabilizer. In some embodiments, a composition as described herein comprises sincalide and a stabilizer (e.g., sodium metabisulfite), wherein the composition does not contain (i.e., lacks) a buffer (e.g., dibasic potassium phosphate) and optionally also does not contain a surfactant/solubilizer (e.g., polysorbate 20), and wherein the composition is storage stable.

Pentetic acid (DTPA) an antioxidant stabilizer, may also act as a chelator. Another non-limiting example of a chelator includes edetic acid (EDTA). In some embodiments, a solid composition as described herein comprises sincalide and chelator (e.g., pentetic acid), wherein the composition does not contain (i.e., lacks) a buffer (e.g., dibasic potassium phosphate) and optionally also does not contain a surfactant/solubilizer (e.g., polysorbate 20), and wherein the composition is storage stable. In some embodiments, a solid composition as described herein comprises sincalide and a stabilizer (e.g., sodium metabisulfite and/or pentetic acid), wherein the composition does not contain (i.e., lacks) a buffer (e.g., dibasic potassium phosphate) and optionally also does not contain a surfactant/solubilizer (e.g., polysorbate 20), and wherein the composition is storage stable.

Amino acids have also been used as stabilizers or co-stabilizers of peptides to: act as cryoprotectants during freeze drying, stabilize against heat denaturation, inhibit aggregate formation, improve solubility or rehydration, inhibit isomerization, reduce surface adsorption, or act as chelating agents. They can also increase the product glass transition temperature ($T_g$) and thereby increase process stability, as well as stabilize the product by minimizing overdrying during secondary drying. Surface exposed residues can react readily with oxidizing agents at physiological pH, scavenging oxidizing molecules and protecting critical regions of peptides.

Various D- and/or L-amino acids can be used as stabilizers in sincalide formulations. As used herein "amino acid(s)" and the names of specific amino acids (e.g., arginine, lysine, methionine, etc.) encompass D- and/or L-amino acids, amino acid salts, derivatives, homologs, dimers, oligomers, or mixtures thereof. Preferred amino acids for use as stabilizers in the present invention include methionine, lysine, and arginine. Examples of other amino acids (and amino acid salts) suitable as stabilizers include, but are not limited to, arginine glutamate, asparagine, gamma aminobutyric acid, glycine, glutamic acid, glutamate, sodium glutamate, histidine, lysine glutamate, lysine aspartate, arginine aspartate, imidazole, serine, threonine, alanine, polyglutamic acid, polylysine, glycylglycine and the like, including hydroxypropyl and galactose derivatives. In preferred embodiments, L-arginine monohydrochloride, L-methionine and L-lysine monohydrochloride are used. In some embodiments, a solid composition as described herein comprises sincalide, a stabilizer (e.g., sodium metabisulfite, L-arginine monohydrochloride, L-methionine and/or L-lysine monohydrochloride), and a chelator (e.g., pentetic acid), wherein the composition does not contain (i.e., lacks) a buffer (e.g., dibasic potassium phosphate) and optionally also does not contain a surfactant/solubilizer (e.g., polysorbate 20), and wherein the composition is storage stable.

Bulking Agents/Tonicity Adjusters

Bulking agents/tonicity adjusters are useful to provide structure and support for the active ingredient, sincalide, as well as to provide tonicity. Bulking agents/tonicity adjusters (also called lyophilization aids) useful in the preparation of lyophilized formulations described herein are known in the art and include mannitol, lactose, potassium chloride, sodium chloride, maltose, sucrose, PEG's (such as, for example, PEG 300, PEG 400, PEG 3350, PEG 6000, PEG 8000 and the like, etc.), trehalose, raffinose, dextrose, polygalacturonic acid galacturonic acid, amino acids (including amino acid salts) such as lysine, arginine, glycine, galactose, etc.), cyclodextrins, such as hydroxypropyl-γ-cyclodextrin (HP-γ-CD), dextran, Ficoll, and polyvinylpyrrolidone (PVP). Of these, D-mannitol is a preferred bulking agent/ tonicity adjuster for use with the compositions described herein. In some embodiments, a composition as described herein comprises sincalide and a bulking agent/tonicity adjuster (e.g., D-mannitol), wherein the composition does not contain (i.e., lacks) a buffer (e.g., dibasic potassium phosphate) and optionally also does not contain a surfactant/solubilizer (e.g., polysorbate 20), and wherein the composition is storage stable. In some embodiments, a composition as described herein comprises sincalide, a stabilizer (e.g., sodium metabisulfite, pentetic acid, L-arginine monohydrochloride, L-methionine and/or L-lysine monohydrochloride), and a bulking agent/tonicity adjuster (e.g., D-mannitol), wherein the composition does not contain (i.e., lacks) a buffer (e.g., dibasic potassium phosphate) and optionally also does not contain a surfactant/solubilizer (e.g., polysorbate 20), and wherein the composition is storage stable. In some embodiments, a composition as described herein comprises sincalide, a stabilizer (e.g., sodium metabisulfite, L-arginine monohydrochloride, L-methionine and/or L-lysine monohydrochloride), a chelator (e.g., pentetic acid), and a bulking agent/tonicity adjuster (e.g., D-mannitol), wherein the composition does not contain (i.e., lacks) a buffer (e.g., dibasic potassium phosphate) and optionally also does not contain a surfactant/solubilizer (e.g., polysorbate 20), and wherein the composition is storage stable.

Cryoprotectants/Lyoprotectants

Various cryoprotectants/lyoprotectants may also be used in the present invention, particularly for lyophilized formulations. Suitable cryoprotectants structure water molecules such that the freezing point is reduced and/or the rate of cooling necessary to achieve the vitreous phase is reduced. They also raise the glass transition temperature range of the vitreous state. These include, but are not limited to: dimethylsulfoxide (DMSO), dextran, sucrose, 1,2-propanediol, amino acids/salts such as, glycine, lysine, arginine, aspartic acid, histidine, proline, etc., glycerol, sorbitol, sodium chloride, fructose, trehalose, raffinose, stachychose, propylene glycol, 2,3-butanediol, hydroxyethyl starch, polyvinylpyrrolidone (PVP), PEG's and similar compounds, protein stabilizers, such as human serum albumin, bovine serum albumin, bovine gamma globulin, gelatin (or derivatives, such as Prionex, etc.), dextrose, glucose, maltose, arabinose, lactose, inositol, polyols (such as sorbitol, xylitol, erithritol, glycerol, ethylene glycol, etc.), tetramethylglucose, sodium sulfate, cyclodextrins and combinations thereof. Lysine and arginine are preferred cryoprotectants/lyoprotectants.

Other Excipients

Other excipients, which may optionally be used in the formulations of the invention include preservatives (e.g., benzalkonium chloride), osmolality adjusters (e.g., dextrose), lyoprotectants (e.g., sodium sulfate), tonicity adjusters (e.g., sodium chloride), cake forming agents, complexing agents, and dissolution aids. A listing of various excipients that can be used in sincalide formulations for parenteral administration can be found in, for example, The Handbook of Pharmaceutical Additives, Second Edition, edited by Michael & Irene Ash; Remington's Pharmaceutical Sciences, (18$^{th}$ Edition), edited by A. Gennaro, 1990, Mack Publishing Company, Easton, Pa. and Pollock el al.; Strickly, Robert G., Parenteral Formulations of Small Molecules Therapeutics Marketed in the United States (1999)—Part I, PDA Journal of Pharmaceutical Science and Technology, 53(6):324 (1999); Strickly, Robert G., Parenteral Formulations of Small Molecules Therapeutics Marketed in the United States (1999)—Part II, PDA Journal of Pharmaceutical Science and Technology, 54(1):69 (2000); Parenteral Formulations of Small Molecules Therapeutics Marketed in the United States (1999)—Part III, PDA Journal of Pharmaceutical Science and Technology, 54(2): 154 (2000); Nema, Sandeep, et al., Excipients and Their Use in Injectable Products, PDA Journal of Pharmaceutical Science and Technology, 51(4): 166 (1997); Wang, Y. J., et al., Parenteral Formulations of Proteins and Peptides: Stability and Stabilizers (Technical Report No. 10), Journal of Parenteral Science and Technology, Vol. 42 (2S), Supplement 1988; Carpenter, J. el al., Freezing- and Drying-Induced Perturbations of Protein Structure and Mechanisms of Protein Protection by Stabilizing Additives, in Drugs and The Pharmaceutical Sciences, Louis Rey and Joan C. May., eds., Marcel Dekker, Inc. New York, N.Y. (1999); Michael J. Pikal, Mechanisms of Protein Stabilization During Freeze-Drying and Storage: The Relative Importance of Thermodynamic Stabilization and Glassy State Relaxation Dynamics, in Drugs and The Pharmaceutical Sciences, Louis Rey and Joan C. May., eds., Marcel Dekker, Inc. New York, N.Y. (1999); Shah, D., et al., The Effects of Various Excipients on the Unfolding of Basic Fibroblast Growth Factor, PDA Journal of Pharmaceutical Science & Technology, 52(5):238 (1998); Powell, M. F., el al., Compendium of Excipients for Parenteral Formulations, PDA Journal of Pharmaceutical Science & Technology, 52(5):238 (1998); and Inactive Ingredient Guide, Div. Of Drug Information Resources, FDA, CDER, January 1996; Handbook of Injectable Drugs, Edition 8, *Am. Soc. Hosp. Pharm.*, 1994, L. A. Trissel.

Tables 1 and 2 provide exemplary non-limiting examples of concentration ranges for sincalide and excipients in solid, liquid, ready-to-use, ready-to-dilute sincalide formulations, or formulations reconstituted from solid sincalide dosage forms lacking a buffer (Table 1) or lacking a buffer and lacking a surfactant/solubilizer (Table 2) described herein.

TABLE 1

| | No Buffer | | | |
|---|---|---|---|---|
| | Formulation 1B | | Formulation 2B | |
| Ingredients | Qty/mL | Qty/vial | Qty/mL | Qty/vial |
| Sincalide | 1 to 5 mcg | 2.5 to 10 mcg | 2.5 mcg | 5 mcg |
| Mannitol | 34 to 170 mg | 85 to 340 mg | 85 mg | 170 mg |
| Arginine Hydrochloride | 6 to 30 mg | 15 to 45 mg | 15 mg | 30 mg |
| Lysine Hydrochloride | 3 to 15 mg | 7.5 to 30 mg | 7.5 mg | 15 mg |
| L-Methionine | 0.8 to 5 mg | 2 to 8 mg | 2 mg | 4 mg |
| Pentetic acid | 0.4 to 5 mg | 1 to 4 mg | 1 mg | 2 mg |
| Sodium Metabisulfite | 0.008 to 1 mg | 0.02 to 1 mg | 0.02 mg | 0.04 mg |
| Potassium phosphate dibasic | N/A | N/A | NA | NA |
| Polysorbate 20 | 0.00125 mcg | 0.005 mcg | 0.0025 mcg | 0.005 mcg |
| Hydrochloric acid/Sodium hydroxide | q.s for pH adjustment to 6.5 to 7.5 | | | |
| Water for Injection* | q.s to 1 mL | q.s to 2 mL | q.s to 1 mL | q.s to 2 mL | q.s: quantity sufficient,
NA: Not applicable.
Qty = Quantity.
*Water for Injection is used as a solvent during manufacture of bulk solution and is removed during lyophilization.

TABLE 2

| | No Buffer or Surfactant/Solubilizer | | | |
|---|---|---|---|---|
| | Formulation 3BS | | Formulation 4BS | |
| Ingredients | Qty/mL | Qty/vial | Qty/mL | Qty/vial |
| Sincalide | 1 to 5 mcg | 2.5 to 10 mcg | 2.5 mcg | 5 mcg |
| Mannitol | 34 to 170 mg | 85 to 340 mg | 85 mg | 170 mg |
| Arginine Hydrochloride | 6 to 30 mg | 15 to 45 mg | 15 mg | 30 mg |
| Lysine Hydrochloride | 3 to 15 mg | 7.5 to 30 mg | 7.5 mg | 15 mg |
| L-Methionine | 0.8 to 5 mg | 2 to 8 mg | 2 mg | 4 mg |
| Pentetic acid | 0.4 to 5 mg | 1 to 4 mg | 1 mg | 2 mg |
| Sodium Metabisulfite | 0.008 to 1 mg | 0.02 to 1 mg | 0.02 mg | 0.04 mg |
| Potassium phosphate dibasic | N/A | N/A | N/A | N/A |
| Polysorbate 20 | N/A | N/A | NA | NA |
| Hydrochloric acid/Sodium hydroxide | q.s for pH adjustment to 6.5 to 7.5 | | | |
| Water for Injection* | q.s to 1 mL | q.s to 2 mL | q.s to 1 mL or 1 L** | q.s to 2 mL | q.s: quantity sufficient,
NA: Not applicable.
Qty = Quantity
*Water for Injection is used as a solvent during manufacture of bulk solution and is removed during lyophilization. One liter may be used in formulating the ready-to-use formulations, which will not be lyophilized.

Storage Stable

A "storage stable" composition refers to a composition that is stable in storage and may be a solid (e.g., lyophilized) formulation. Such "storage stable" compositions may also refer to ready-to-use or ready-to-dilute aqueous (e.g., liquid) compositions that are stable in storage. Such storage stable compositions refer to those in which the composition maintains sincalide in its active form and/or has a limited amount of impurities and/or maintains the pH within the desired range upon storage at a selected temperature for a selected time period.

For example, a composition is considered stable under certain conditions so long as the composition retains at least 90% of its active sincalide and/or total impurities remain less than 5% of the total composition (or no individual impurity exceeds 1% of the total composition and/or the total impurities increase by no more than 3-5%). In some embodiments, a composition is considered stable so long as the composition retains at least 95% of its active sincalide. In some embodiments, a composition is considered stable so long as the composition retains at least 95% or 99% of its active sincalide. In some embodiments, a composition is considered stable so long as total impurities remain less than 5% of the composition. In some embodiments, a composition is considered stable so long as total impurities remain less than 4% of the composition. In some embodiments, a composition is considered stable so long as total impurities remain less than 3%, 2.5% or 2.0% of the composition. In some embodiments, a composition is considered stable so long as no individual impurity makes up more than 1% of the composition. In some embodiments, a composition is considered stable so long as no individual impurity makes up more than 1.5% of the composition. In some embodiments, a composition is considered stable so long as the initially adjusted pH remains within ±1.0 pH unit. In some embodiments, a composition is considered stable so long as the initially adjusted pH remains within ±0.75 pH units. In some embodiments, a composition is considered stable so long as the initially adjusted pH remains within ±0.5 pH units. In some embodiments, a composition is considered stable so long as the initially adjusted pH remains within ±0.25 pH units. "Shelf-life" refers to the amount of time a composition remains stable under certain conditions.

For accelerated screening of the stability and/or shelf-life of a composition, a composition to be approved for storage at room temperature (e.g., a solid sincalide composition) may be kept under accelerated screening conditions at 40° C. and 75% relative humidity (RH) for at least 2 weeks to the end of its shelf-life (e.g., about 6 months) under those conditions, during which individual components of the compositions may be measured at different timepoints including immediately after formulation and/or just prior to lyophilization, e.g., 2 weeks, 1 month, 2 months, 3 months, 4 months, 5 months and/or 6 months.

For physicochemical characterizations, a composition may be stored at 25° C. at 60% RH for at least one hour to the end of its shelf-life under those conditions, during which individual components of the composition may be measured at different timepoints, including immediately after formulation and/or just prior to lyophilization, and 1 hour, 2 hours, 4 hours, 6 hours, 8 hours, 16 hours, 24 hours, 1 week, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months and/or 24 months after formulation or lyophilization.

Where the formulation is to be approved for refrigerated storage (e.g., a liquid sincalide composition), the composition may be stored long-term, e.g., at 2-8° C., and individual components of the composition may be measured at different timepoints, including immediately after formulation and/or just prior to lyophilization, and 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months and/or 36 months after formulation or lyophilization. The active form of sincalide and/or impurities may be measured by a sincalide-specific assay, e.g., a chromatography method, e.g., high performance liquid chromatography (HPLC).

Generally, the compositions described herein are stable with regard to retention of the active form of sincalide activity and/or with regard to reduced levels of impurities after storage, e.g., are storage stable.

In some embodiments, a lyophilized composition comprising sincalide and lacking a buffer (and optionally further lacking a surfactant/solubilizer) as described herein has a shelf-life (the composition comprises less than 5%, less than 4%, less than 3%, less than 2.5%, and/or less than 2% total impurities, retains at least 90,% or 95% of active sincalide, and/or no individual impurity makes up more than 2%, 1.5% or 1% of the composition) of at least 15 months, or 18 months, or 21 months, or 24 months, or 36 months when stored at 25° C. and 60% relative humidity. In some embodiments, a lyophilized composition comprising sincalide and lacking a buffer (and optionally further lacking a surfactant/solubilizer) as described herein has a shelf-life (the composition comprises less than 5%, less than 4%, less than 3%, less than 2.5%, and/or less than 2% total impurities, retains at least 90% or 95% of active sincalide, no individual impurity makes up more than 2%, 1.5% or 1% of the composition, and/or the percentage of impurities increases by nor more than 3-4%) of at least 3 months when stored at 40° C. and 75% relative humidity. In some embodiments, a lyophilized composition comprising sincalide and lacking a buffer (and optionally further lacking a surfactant/solubilizer) as described herein has a shelf-life (the composition comprises less than 6%, less than 5%, less than 4%, less than 3%, less than 2.5%, and/or less than 2% total impurities, retains at least 85, 90% or 95% of active sincalide, no individual impurity makes up more than 2%, 1.5% or 1% of the composition, and/or the percentage of impurities increases by nor more than 4-5%) of at least 6 months when stored at 40° C. and 75% relative humidity.

In some embodiments, a ready-to-use liquid composition comprising sincalide (and optionally lacking a buffer and optionally also lacking a surfactant/solubilizer) as described herein has a shelf-life (the composition comprises less than 5%, less than 4%, less than 3%, less than 2.5%, and/or less than 2% total impurities, retains at least 90% or 95% of active sincalide, and/or no individual impurity makes up more than 2%, 1.5% or 1% of the composition) of at least 12 months, 15 months, or 18 months, or 21 months, or 24 months, or 36 months when stored at 2-8° C. In some embodiments, a ready-to-use liquid composition comprising sincalide (and optionally lacking a buffer and optionally also lacking a surfactant/solubilizer) as described herein has a shelf-life (the composition comprises less than 5%, less than 4%, less than 3%, less than 2.5%, and/or less than 2% total impurities, retains at least 90% or 95% of active sincalide, no individual impurity makes up more than 2%, 1.5% or 1% of the composition, and/or the percentage of impurities increases by nor more than 2-3%) of at least 6 months when stored at 25° C. and 60% relative humidity.

In some embodiments, a ready-to-use composition comprising sincalide and lacking a buffer as described herein has a shelf-life (the composition comprises less than 10%, less than 6%, and/or less than 5% total impurities, and/or retains at least 90% or 95% of active sincalide) of at least 12 months, 15 months, 21 months, or 24 when stored at 25° C. and 60% relative humidity.

Methods of Making

Lyophilized formulations which lack a buffer (e.g., phosphate or dibasic potassium phosphate buffers) and optionally lack a surfactant/solubilizer (e.g., polysorbate 20 or polysorbate 80) are made according to a method comprising dissolving the ingredients (e.g., sincalide and excipients comprising a stabilizer and/or a bulking agent/tonicity adjuster, and optionally a surfactant/solubilizer; or e.g., sincalide and excipients consisting essentially of a stabilizer and/or a bulking agent/tonicity adjuster, and optionally a surfactant/solubilizer) in Water for Injection. The method may further comprise adjusting the pH to 6 to 8, e.g., 6.5 to 7.5 with a pH adjuster (e.g., sodium hydroxide and/or hydrochloric acid) and sterilizing the solution (e.g., by filtration through a 0.22 micron membrane sterilizing grade filter).

For lyophilized formulations, the solution may be filled into vials, e.g., 5 mL Type I glass vials) to an appropriate volume, e.g., about 2 mL, stoppered (e.g., with chlorobutyl or bromobutyl or rubber stoppers) and lyophilized. Optionally, the lyophilized formulations may be stoppered under a vacuum, wherein the vacuum is adjusted with nitrogen prior to stoppering.

For ready-to-use formulations, the compositions are prepared by dissolving the ingredients (e.g., sincalide and excipients comprising a stabilizer and/or a bulking agent/tonicity adjuster, and optionally a buffer, and optionally a surfactant/solubilizer) in Water for Injection. The method may further comprise adjusting the pH to 6 to 8, e.g., 6.5 to 7.5 with a pH adjuster (e.g., sodium hydroxide and/or hydrochloric acid) and sterilizing the solution (e.g., by filtration through a 0.22 micron membrane sterilizing grade filter). The pH adjusted liquid is then packaged for use and appropriate dilution prior to administration.

Therapeutic/Diagnostic Uses

Sincalide is a synthetic analog of the endogenously produced hormone cholecystokinin (CCK-8). CCK-8 acts on receptors within the gallbladder wall causing it to contract, cleaning out any remaining sludge or bile that may have accumulated within the gallbladder. CCK-8 increases bile flow and small and large bowel motility, causes the pyloric sphincter to contract and increases pancreatic enzyme secretion. CCK-8 also causes delayed biliary to bowel transit. Sincalide has a more rapid physiologic effect on the gallbladder in terms of contraction and relaxation than the endogenous hormone (CCK-8) produced by the body, making sincalide formulations useful as diagnostic aids for hepatobiliary imaging, when administered alone or in conjunction with a hepatobiliary imaging agent. For example, sincalide may be administered before and/or after diagnostic imaging (such as, for example, magnetic resonance imaging, scintigraphic imaging, ultrasound imaging, etc.) to improve visualization and/or diagnosis of various disease states.

Accordingly, provided herein are methods for the treatment, prevention, and/or diagnosis of gall bladder- and/or pancreatic disorders; or other diagnostic imaging in a patient in need thereof comprising administering to the patient a pharmaceutical sincalide composition comprising a therapeutically effective amount of sincalide and a pharmaceutically acceptable carrier, wherein the solid composition. (i) does not contain a buffer having a pKa within one unit of a desired pH; or (ii) neither contains a such a buffer nor a surfactant/solubilizer. Ready-to-use or ready-to-dilute formulations may contain or lack a buffer having a pKa within one unit of a desired pH; and also may contain or lack a surfactant/solubilizer.

Administration of sincalide formulations can be via IV or IM injections. For IV administration, the dose can be administered as a bolus or slow injection over time optionally with the aid of an infusion pump. The dose for IV administration is typically 0.005 to 0.04 µg/kg (bolus injection) or 0.005 µg/kg in a series of 4 three-minute injections. A dose of 0.02-0.04 µg/kg IV over 2-3 minutes, but up to 1 hour is described in the art. Injection rates of 0.58 µg/kg/hour can also be employed with the use of an infusion pump. Other regimens starting at 10 ng/kg/hr and increasing to 160 ng/kg/hr are also known in the art. Bolus injection is not recommended in every case, but injection of 0.02 to 0.04 µg/kg over 2-3 minutes even up to 15 min. can be used to avoid spasm of the cystic duct or gall bladder.

Doses for IM administration are generally higher and range from 0.1 to 0.4 µg/kg. In one embodiment the 0.4 µg/kg IM dose is generally preferred resulting in the greatest gallbladder response with the fewest side effects. Further details on administration are provided in, for example, Mesgarzadeh M., et al., Filling, post cholecystokinin emptying and refilling of normal gallbladder: effects of two different doses of CCK on refilling, *J. Nucl. Med.*, (1983), 24:666-671; Ziessmann H A., et al., Calculation of a gallbladder ejection fraction: Advantage of continuous sincalide infusion over the three-minute infusion method. *J. Nucl. Med.*, (1992), 33:537-541; Pickleman J, et al., The role sincalide cholescintigraphy in the evaluation of patients with acalculous gallbladder disease, *Arch. Surg.*, vol. 120, 693-697; Krishnamurthy G T., et al., The gallbladder emptying response to sequential exogenous cholecystokinin, *Nucl. Med. Com.*, (1984), 5(1) pp 27-33; Krishnamurthy G T., et al., Quantitative biliary dynamics: introduction of a new noninvasive scintigraphic technique. *J. Nucl. Med.*, (1983), 24:217-223; Fink-Bennet D., The role of cholecystogogues in the evaluation of biliary tract disorders, *Nucl. Med. Ann.*, (1985), Lenny Freeman and Heidi Weissman, eds., New York, Raven Press, (1985), 107-132; Balon H. R., et al., Society of Nuclear Medicine procedure guideline for hepatobiliary scintigraphy.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

05-183, B. size: 7.0 L was manufactured in a production line. The filled vials (target fill volume 2.05 mL) were loaded into a production lyophilizer and lyophilized. At the end of the lyophilization cycle, the vials were stoppered under vacuum, n and then sealed. The concentrations of the ingredients of the sincalide formulations used in these experiments are provided in Table 3.

TABLE 3

| Ingredients | Batch SCL-05-048 Devoid of buffer | | Batch SCL-05-042; SCL-05-183 Devoid of buffer and polysorbate 20 | | Batch SCL-07-116 Devoid of buffer and polysorbate 20 | |
|---|---|---|---|---|---|---|
| | Qty/mL | Qty/vial | Qty/mL | Qty/vial | Qty/mL | Qty/vial |
| Sincalide | 2.5 mcg | 5 mcg | 2.5 mcg | 5 mcg | 2.5 mcg | 5 mcg |
| Mannitol | 85 mg | 170 mg | 85 mg | 170 mg | 85 mg | 170 mg |
| Arginine HCl | 15 mg | 30 mg | 15 mg | 30 mg | 15 mg | 30 mg |
| Lysine HCl | 7.5 mg | 15 mg | 7.5 mg | 15 mg | 7.5 mg | 15 mg |
| L-Methionine | 2 mg | 4 mg | 2 mg | 4 mg | 2 mg | 4 mg |
| Pentetic acid | 1 mg | 2 mg | 1 mg | 2 mg | 1 mg | 2 mg |
| Sodium Metabisulfite | 0.02 mg | 0.04 mg | 0.02 mg | 0.04 mg | 0.02 mg | 0.04 mg |
| Potassium phosphate dibasic | NA | NA | NA | NA | NA | NA |
| Polysorbate 20 | 0.0025 mcg | 0.005 mcg | NA | NA | NA | NA |
| HCl/NaOH | | | q.s for pH adjustment to 6.5 to 7.5 | | | |
| Water for Injection* | q.s to 1 mL | q.s to 2 mL | q.s to 1 mL | q.s to 2 mL | q.s. to 1 mL | q.s. to 2 mL |

EXAMPLES

The following examples are provided for illustrative purposes only and do not limit the scope of the invention.

Example 1: Preparation of Solid Sincalide Formulations and Comparison with KINEVAC®

Lab batches of Sincalide for Injection formulation bulk solutions at a concentration of 2.5 mcg/mL, Batch No. SCL-05-042, B. Size: 750 mL (without buffer and polysorbate 20) and Batch No.: SCL-05-048, B. Size: 750 mL (without buffer) were manufactured by dissolving the ingredients in Water for Injection, and adjusting the pH to 6.5 to 7.5 with sodium hydroxide and/or hydrochloric acid. The bulk solutions were filtered through 0.22 μm membrane filter and filled into 5 mL Type I glass vials with fill volume of 2.10 mL and half stoppered with chlorobutyl rubber stoppers. The filled vials were loaded into a lyophilizer maintained at 5° C. and lyophilized. At the end of the lyophilization cycle, the vials were stoppered under vacuum, and then sealed.

A pilot-scale batch of Sincalide for Injection bulk solution, at a concentration of 2.5 mcg/mL; Batch. No.: SCL- Example 2: Assay of Sincalide and Related Substances The Assay of Sincalide in the drug product is determined through a high-performance liquid chromatography (HPLC) method utilizing a reverse phase column with a trifluoro acetic acid, water and acetonitrile mobile phase gradient and a UV photodiode array detector (PDA), and quantitated against a sincalide.

The Related Substances of Sincalide in the drug product are determined through an HPLC method utilizing a reverse phase column with a trifluoro acetic acid, water and acetonitrile mobile phase gradient and a UV photodiode array detector (PDA), and quantitated as an area %. The term "area percent" refers to the area under the given peak (at a given relative retention time "RRT"), expressed as a percentage of the total area (under) of all the relevant HPLC peaks.

Example 3: Stability of Sincalide Formulations Lacking a Buffer, and Optionally a Surfactant/Solubilizer Compositions consisting of sincalide and sodium chloride (NaCl), see, e.g., U.S. Pat. No. 3,937,819, proved to not be stable in storage. For example, a composition comprising sincalide and NaCl at a pH of 5.5-6.5 demonstrated over 6.5% total impurities after 1 month at 20° C., 2-8° C., or 25° C./60% RH (data not shown). Additionally, the percent of the labeled amount of active sincalide remaining fell to less than 90% after 3 months of storage at −20° C., after 2 months after storage at 2-8° C., or after 1 month after storage at 25° C./60% RH (data not shown).

Such stability issues were allegedly resolved by the compositions described in U.S. Pat. No. 6,803,046, which attributed the stability of the compositions described therein, at least in part, to the use of a buffer and/or surfactant/ solubilizer. When KINEVAC® was tested at its expiration date when stored as a lyophilized powder at 25° C. prior to its testing, KINEVAC® showed greater than 90% of the labeled amount of sincalide and between 2.82% and 6.07% total impurities (data not shown). As a comparison, the stability of a KINEVAC® batch was analyzed four months prior to its labeled expiration date and at its expiration date (Table 4); in addition, the stability of this KINEVAC® batch after 1 month and 3 months of storage under accelerated stability conditions (40° C./75% RH) are also shown. As shown, storage of the lyophilized KINEVAC® powder at 40° C. and 75% relative humidity for prior to its expiration date resulted in a diminished amount of sincalide (85.4%) and increased impurities (5.27%).

TABLE 4

| | KINEVAC ® | | | |
|---|---|---|---|---|
| Test Parameters | 4 mo. prior to ED | At ED | 40° C./75% RH 3 mo. Prior to ED | 40° C./75% RH 1 mo. Prior to ED |
| Assay of Sincalide (% of labelled amount 5 μg/vial) | 95.1% | 97.7% | 91.9% | 85.4% |
| Desulfated Sincalide | BQL | BQL | BQL | BQL |
| Sum of Sincalide related impurities at RRT 0.28 to 0.90 | 2.45 | 3.40 | 3.76 | 4.02 |
| Sum of Sincalide related impurities at RRT >1.0 excluding Desulfated Sincalide | 1.59 | 1.82 | 1.29 | 1.24 |
| Any unspecified impurity | 1.17 | 0.99 | 1.30 | 1.53 |
| Total impurities | 4.05 | 5.22 | 5.05 | 5.27 | mo = month(s).
ED = expiration date

Surprisingly, the compositions used in these examples below (described in Table 3, investigated in Tables 5-8), which do not comprise a buffer, are as stable or more stable than KINEVAC® in storage (Table 4). The KINEVAC® formulation did not maintain the level of sincalide over 90%, and did not maintain the level of total impurities below 5% after the 3 month accelerated stability testing (Table 4), while the formulations described herein show minimal loss of sincalide (maintained above 95%) and improved inhibition of total impurity formation (below 3%) under the same conditions.

The performance of the formulations described herein under long term stability testing (25° C./65% relative humidity) also shows storage stability, with maintenance of sincalide levels above 95%, total impurities below 1.5% and individual impurities below 1% for the duration of the 18-month study (Table 6). In comparison, commercial batches of KINEVAC® show sincalide levels ranging from 94.1% to 101.4% at expiry, individual impurities ranging from 0.93% to 1.71%, and total impurities ranging from 2.82% to 6.07%. Thus, the compositions described herein are storage stable, while the commercial KINEVAC® formulation is not storage stable under these conditions. These determinations demonstrate storage stability for the compositions described herein.

Similarly, the aqueous compositions prepared and analyzed as described herein show storage stability upon accelerated (25° C./65% relative humidity) and long term (2°-8° C. storage), see Tables 7 and 8, respectively. Sincalide assays show retention of the active ingredient to levels above 95%, inhibition of total impurity levels below 2.5%, and individual impurities below 2% for each of the storage conditions

TABLE 5

| | 40 C./75% RH Accelerated Data-Inverted Configuration | | | | | | | | | | |
|---|---|---|---|---|---|---|---|---|---|---|---|
| | Devoid of Buffer [Batch No.: SCL-05-048] | | | | | Devoid of Buffer and Surfactant/Solubilizer [Batch Nos.: SCL-05-042; (SCL-05-183)] | | | | | KINEVAC ® |
| Attributes | Initial | 1 mo | 2 mo | 3 mo | 6 mo | Initial | 1 mo | 2 mo | 3 mo | 6 mo | 3 mo |
| pH | 6.8 | 6.8 | 6.9 | 6.9 | NP | 6.8 (7.0) | 6.9 (7.0) | 6.9 (7.0) | 6.9 (7.1) | NP (7.0) | NP |
| Assay of Sincalide (% labeled amount: 5 mcg/vial) | 101.3 | 106.1 | 91.1 | 96.8 | 88.7 | 104.9 (101.1) | 108.3 (103.1) | 97.3 (99.1) | 101.8 (94.0) | 92.2 (94.4) | 85.4 |
| | Related Substances (%) | | | | | | | | | | |
| Desulfated Sincalide (%) | BQL | BQL | BQL | 0.10 | 0.15 | BQL (BQL) | BQL (BQL) | 0.11 (0.12) | 0.12 (0.15) | 0.21 (0.12) | BQL |
| Sum of Sincalide-related impurities at RRT 0.28 to 0.90 (%) | 0.40 | 0.58 | 1.75 | 1.32 | 3.19 | 0.46 (1.77) | 0.48 (0.70) | 1.52 (1.30) | 1.54 (2.16) | 2.80 (3.74) | 4.02 |
| Sum of Sincalide-related impurities at RRT >1.0 excl. | BQL | 0.19 | 0.20 | 0.82 | 2.15 | 0.12 (BQL) | 0.46 (0.24) | 0.88 (0.49) | 0.73 (0.75) | 1.75 (1.00) | 1.24 |

TABLE 5-continued

| | 40 C./75% RH Accelerated Data-Inverted Configuration | | | | | | | | | | |
|---|---|---|---|---|---|---|---|---|---|---|---|
| | Devoid of Buffer [Batch No.: SCL-05-048] | | | | | Devoid of Buffer and Surfactant/Solubilizer [Batch Nos.: SCL-05-042; (SCL-05-183)] | | | | | KINEVAC ® |
| Attributes | Initial | 1 mo | 2 mo | 3 mo | 6 mo | Initial | 1 mo | 2 mo | 3 mo | 6 mo | 3 mo |
| Desulfated Sincalide (%) | | | | | | | | | | | |
| Any unspecified impurity (%) | 0.40 | 0.41 | 1.08 | 0.67 | 1.35 | 0.33 (1.04) | 0.48 (0.41) | 0.94 (0.75) | 0.77 (1.15) | 1.28 (1.97) | 1.53 |
| Total impurities (%) | 0.40 | 0.78 | 1.96 | 2.24 | 5.61 | 0.58 (1.77) | 0.94 (0.94) | 2.51 (1.92) | 2.39 (3.06) | 4.91 (4.86) | 5.27 |

NP = not performed.
BQL = Below quantification limit.

TABLE 6

| | Devoid of buffer and surfactant/solubilizer (SCL-05-183)] 25° C./60% RH, Inverted | | | | | | | |
|---|---|---|---|---|---|---|---|---|
| Test parameters | Initial | 1 month | 2 months | 3 months | 6 months | 9 months | 12 months | 18 months |
| Description | A white lyophilized cake | A white lyophilized cake | A white lyophilized cake | A white lyophilized cake | A white lyophilized cake | A white lyophilized cake | A white lyophilized cake | A white lyophilized cake |
| pH | 7.0 | 7.0 | 7.0 | 7.0 | 7.0 | 7.0 | 7.0 | 7.0 |
| Assay of Sincalide (% of labeled amount: 5 mcg/vial) | 101.1% | 105.1% | 103.8% | 100.3% | 104.8% | 98.7% | 97.7% | 100.5% |
| Related Substances by HPLC | | | | | | | | |
| Desulfated Sincalide | BQL | BQL | BQL | BQL | BQL | BQL | BQL | BQL |
| Sum of Sincalide related impurities at RRT 0.28 to 0.90 | 1.77% | 0.16% | 0.27% | 0.24% | 0.74% | 0.60% | 0.50% | 0.86% |
| Sum of Sincalide related impurities at RRT >1.0 excluding Desulfated Sincalide | BQL | 0.13% | BQL | BQL | BQL | 0.10% | BQL | 0.33% |
| Any unspecified impurity | 1.04% | 0.16% | 0.27% | 0.24% | 0.29% | 0.44% | 0.25% | 0.46% |
| Total impurities | 1.77% | 0.30% | 0.27% | 0.24% | 0.74% | 0.70% | 0.50% | 1.19% |

BQL = Below quantification limit.

TABLE 7

2.5 mcg/mL Aqueous Liquid Formulation-Sincalide Without Buffer and Polysorbate 20 (SCL-07-116)

Condition: 25° C./60% RH Accelerated Data

| Batch Details | | | | | | | | | |
|---|---|---|---|---|---|---|---|---|---|
| Orientation | | Upright | | | | | Invert | | |
| Time Point | Initial | 1 mo | 2 mo | 3 mo | 6 mo | 1 mo | 2 mo | 3 mo | 6 mo |
| Description | A clear colorless solution | A clear colorless solution | A clear colorless solution | A clear colorless solution | A clear colorless solution | A clear color solution | A clear colorless solution | A clear colorless solution | A clear colorless solution |
| pH | 7.0 | 7.0 | 7.0 | 7.0 | 7.0 | 7.0 | 7.0 | 7.0 | 7.0 |
| Assay (% of Initial) | 100.0% | 104.6% | 103.9% | 99.9% | 100.0% | 105.3% | 102.9% | 101.1% | 99.8% |
| Related Substances | | | | | | | | | |
| Desulfated Sincalide | BQL | BQL | BQL | BQL | BQL | BQL | BOL | BQL | BQL |
| Sum of Sincalide related impurities at RRT 0.28 to 0.90 | 0.25% | 0.55% | 0.84% | 1.14% | 2.20% | 0.79% | 0.90% | 1.12% | 2.38% |
| Sum of Sincalide related impurities at RRT.1.0 excluding desulfated sincalide | ND | ND | ND | ND | ND | ND | ND | ND | ND |
| Any unspecified impurity | 0.25% | 0.28% | 0.55% | 0.83% | 1.71% | 0.53% | 0.58% | 0.81% | 1.75% |
| Total impurities | 0.25% | 0.55% | 0.84% | 1.14% | 2.20% | 0.79% | 0.89% | 1.12% | 2.38% |

M = month(s).
BQL = Below quantification limit.
ND = not detected.

TABLE 8

2.5 mcg/mL Liquid Formulation-Sincalide Without Buffer and Polysorbate 20 (SCL-07-116)

Condition: 2° C.-8° C. long-term stability data

| Batch Details | | | | | | | |
|---|---|---|---|---|---|---|---|
| Orientation | | Upright | | | | Invert | |
| Time Point | Initial | 3 mo | 6 mo | 12 mo | 3 mo | 6 mo | 12 mo |
| Description | A clear colorless solution | A clear colorless solution | A clear colorless solution | A clear colorless solution | A clear colorless solution | A clear colorless solution | A clear colorless solution |
| pH | 7.0 | 7.0 | 7.0 | 6.8 | 7.0 | 7.0 | 6.8 |
| Assay (% of Initial) | 100.0% | 99.6% | 102.2% | 102.1% | 1015% | 102.1% | 104.7% |
| Related substances | | | | | | | |
| Desulfated Sincalide (RRT 1.11) | BQL | BQL | BQL | BQL | BQL | BQL | BQL |
| Sum of Sincalide related impurities at RRT 0.28 to 0.90 | 0.25% | 0.21% | 0.29% | 0.69% | 0.30% | 0.28% | 0.55% |
| Sum of Sincalide related impurities at RRT.1.0 excluding desulfated sincalide | ND | ND | ND | BQL | ND | ND | BQL |

TABLE 8-continued

| Batch Details Condition | 2.5 mcg/mL Liquid Formulation-Sincalide Without Buffer and Polysorbate 20 (SCL-07-116) 2° C.-8° C. long-term stability data | | | | | | |
|---|---|---|---|---|---|---|---|
| Orientation | Upright | | | | Invert | | |
| Time Point | Initial | 3 mo | 6 mo | 12 mo | 3 mo | 6 mo | 12 mo |
| Any unspecified impurity | 0.25% | 0.21% | 0.29% | 0.47% | 0.30% | 0.28% | 0.32% |
| Total impurities | 0.25% | 0.21% | 0.29% | 0.69% | 0.30% | 0.28% | 0.55% |

M = month(s).
BQL = Below quantification limit.
ND = not detected.

As demonstrated by the examples provided above, the solid compositions described herein are as stable as or more stable than the marketed KINEVAC® formulations.

Additionally, and also surprisingly, the liquid formulations described herein are storage stable under all tested stability conditions.

What is claimed is:

1. A liquid composition comprising:
(a) from 1 to 5 μg/mL of sincalide;
(b) from 0.4 to 5 mg/mL of pentetic acid;
(c) from 6 to 30 mg/mL of arginine hydrochloride;
(d) from 0.8 to 5 mg/mL of L-methionine;
(e) from 3 to 15 mg/mL of L-lysine hydrochloride;
(f) from 0.008 to 1 mg/mL of sodium metabisulfite;
(g) from 34 to 170 mg/mL of mannitol; and
(h) a pharmaceutically acceptable carrier,
wherein the pH of the liquid composition is 6.5 to 7.5,
wherein the liquid composition does not contain phosphate buffer, a surfactant, a solubilizer, polysorbate 20, or polysorbate 80, and
wherein the liquid composition maintains total impurities of less than 5% and/or a sincalide level of at least 90% after
i) 6 months of storage at 25° C., 65% relative humidity, or
ii) 12 months of storage at 2-8° C.,
when tested by high-performance liquid chromatography.

2. The liquid composition of claim 1, wherein the liquid composition does not contain a buffer having a pKa within one unit of the pH.

3. The liquid composition of claim 2, wherein the liquid composition does not contain a buffer selected from the group consisting of phosphoric acid, citric acid, citrate, sulfosalicylate, acetic acid, acetate, methyl boronic acid, boronate, disodium succinate hexahydrate, lactic acid, lactate, maleic acid, maleate, potassium chloride, benzoic acid, sodium benzoate, carbonic acid, carbonate, bicarbonate, boric acid, sodium borate, sodium chloride, succinic acid, succinate, tartaric acid, tartrate, tris-(hydroxymethyl)aminomethane, N-2-hydroxyethylpiperazine, N'-2-ethanesulfonic acid, CHAPS, and any combination thereof.

4. The liquid composition of claim 1, wherein the liquid composition does not contain a polysorbate.

5. The liquid composition of claim 1, wherein the liquid composition is ready-to-use.

6. The liquid composition of claim 1, wherein the liquid composition comprises:
(a) 2.5 μg/mL of sincalide;
(b) 1 mg/mL pentetic acid;
(c) 15 mg/mL arginine hydrochloride;
(d) 2 mg/mL methionine;
(e) 7.5 mg/mL lysine hydrochloride;
(f) 0.02 mg/mL sodium metabisulfite; and
(g) 85 mg/mL mannitol.

7. The liquid composition of claim 1, wherein the liquid composition comprises:
(a) 1 μg/mL of sincalide;
(b) 0.4 mg/mL pentetic acid;
(c) 6 mg/mL arginine hydrochloride;
(d) 0.8 mg/mL methionine;
(e) 3 mg/mL lysine hydrochloride;
(f) 0.008 mg/mL sodium metabisulfite; and
(g) 34 mg/mL mannitol.

8. A method comprising administering the liquid composition of claim 1 to the patient.

9. The method of claim 8, further comprising diluting the liquid composition prior to administering it.

10. The method of claim 8, wherein the liquid composition comprises:
(a) 2.5 μg/mL of sincalide;
(b) 1 mg/mL pentetic acid;
(c) 15 mg/mL arginine hydrochloride;
(d) 2 mg/mL methionine;
(e) 7.5 mg/mL lysine hydrochloride;
(f) 0.02 mg/mL sodium metabisulfite; and
(g) 85 mg/mL mannitol.

11. The method of claim 8, wherein the liquid composition comprises:
(a) 1 μg/mL of sincalide;
(b) 0.4 mg/mL pentetic acid;
(c) 6 mg/mL arginine hydrochloride;
(d) 0.8 mg/mL methionine;
(e) 3 mg/mL lysine hydrochloride;
(f) 0.008 mg/mL sodium metabisulfite; and
(g) 34 mg/mL mannitol.

12. The method of claim 8, wherein the liquid composition does not contain a buffer having a pKa within one unit of the pH.

13. The method of claim 12, wherein the liquid composition does not contain a buffer selected from the group consisting of phosphoric acid, citric acid, citrate, sulfosalicylate, acetic acid, acetate, methyl boronic acid, boronate, disodium succinate hexahydrate, lactic acid, lactate, maleic acid, maleate, potassium chloride, benzoic acid, sodium benzoate, carbonic acid, carbonate, bicarbonate, boric acid, sodium borate, sodium chloride, succinic acid, succinate, tartaric acid, tartrate, tris-(hydroxymethyl)aminomethane, N-2-hydroxyethylpiperazine, N'-2-ethanesulfonic acid, CHAPS, and any combination thereof.

14. The method of claim 8, wherein the liquid composition does not contain a polysorbate.

15. A method of making the liquid composition of claim 1 comprising:
  mixing:
   (i) sincalide;
   (ii) pentetic acid;
   (iii) arginine hydrochloride;
   (iv) L-methionine;
   (v) L-lysine hydrochloride;
   (vi) sodium metabisulfite;
   (vii) mannitol;
   (viii) a pH adjuster; and
   (ix) water.

16. The method of claim 15, further comprising filling the liquid composition into a vial.

17. The method of claim 15, wherein the liquid composition is a ready-to-use composition.

18. A kit comprising the liquid composition of claim 1 and a vial, wherein the liquid composition has a volume of 1 to 10 mL.

19. A method of making the kit of claim 18 comprising:
  (a) mixing:
   (i) sincalide;
   (ii) pentetic acid;
   (iii) arginine hydrochloride;
   (iv) L-methionine;
   (v) L-lysine hydrochloride;
   (vi) sodium metabisulfite;
   (vii) mannitol;
   (viii) a pH adjuster;
   (ix) water,
   wherein mixing generates a liquid composition; and
  (b) filling the liquid composition into a vial.

20. The method of claim 8, comprising administering the liquid composition in conjunction with a hepatobiliary imaging agent to the patient.

* * * * *